United States Patent [19]
Bowsman

[11] Patent Number: 5,971,152
[45] Date of Patent: Oct. 26, 1999

[54] CONTAINER WITH REINFORCED TAB AND METHOD

[75] Inventor: Randall J. Bowsman, Walnut, Calif.

[73] Assignee: Ray Products, Inc., Ontario, Calif.

[21] Appl. No.: 09/108,272

[22] Filed: Jul. 1, 1998

[51] Int. Cl.⁶ ..................................................... A61L 2/00
[52] U.S. Cl. ........................... 206/438; 206/370; 206/447; 53/433; 422/300
[58] Field of Search ..................................... 206/438, 439, 206/363, 370, 557, 559–565, 447, 520, 223, 568; 422/300, 297, 310; 220/645, 639, 651, 23.89, 23.87, 528, 675; 264/239, 241; 53/432, 433, 467

[56] References Cited

U.S. PATENT DOCUMENTS

| | | | |
|---|---|---|---|
| 3,416,703 | 12/1968 | Chmielowiec | 220/651 |
| 4,482,053 | 11/1984 | Alpern et al. | 206/439 |
| 4,697,703 | 10/1987 | Will | 206/438 |
| 4,750,619 | 6/1988 | Cohen et al. | 206/438 |
| 5,266,763 | 11/1993 | Colombo | 220/23.87 |
| 5,375,735 | 12/1994 | Huvey et al. | 220/23.87 |
| 5,393,539 | 2/1995 | Reskow | 220/651 |
| 5,441,707 | 8/1995 | Lewis et al. | 206/438 |

*Primary Examiner*—Jacob K. Ackun
*Assistant Examiner*—Luan K. Bui
*Attorney, Agent, or Firm*—D'Alessandro & Ritchie

[57] ABSTRACT

A package having a container having an inner surface, an outer surface, and a sidewall defining a cavity, with the container having an inner locking tab in the cavity defining a recess in the outer surface of the container, and with a stiffening material being placed in the recess to add strength to the locking tab.

23 Claims, 3 Drawing Sheets

CONTAINER WITH REINFORCED TAB AND METHOD

BACKGROUND OF THE INVENTION

1. Field Of The Invention

The present invention relates to packages, and more particularly to sterile packages having a plurality of sterile articles therein. Still more particularly, it relates to the carriage of products within such packages.

2. The Background Art

Sterile packages for retaining a plurality of sterile articles are known. Typically, such packages have a tray with recesses, with the sterile articles being received in the recesses. The recesses are commonly covered with a cover permeable to the passage of a sterilization gas and impermeable to the passage of bacteria. The tray and articles are rendered sterile by passing the sterilization gas through the cover and onto the articles and tray. The covered trays may then be stored and transported while maintaining the sterile barrier in the tray. At the time of a medical procedure, the cover is removed by operating personnel to expose the sterile articles for use in the procedure. For larger sterile articles, a large container may be used with a tray retaining the sterile articles being received in a cavity of the container.

In a suitable form, such containers may be vacuum formed, by a process in which a plastic sheet is clamped to a frame, and the sheet is heated and drawn down into a mold by a vacuum. Since the entire package is preferably disposable, it is desirable to minimize the thickness of its walls in order to reduce the cost and bulk of the container. This also aids in allowing the sheet to conform to the mold. However, the vacuum formed container may have regions of weakness due to a reduced thickness of the wall induced by the vacuum forming process. In this case, the region of weakness may rupture or tear, thus exposing the sterile articles to the atmosphere which may cause contamination of the tray unknown to the attending operating personnel, with possible deleterious results to the patient.

In one form, the plastic sheet and corresponding container walls may be made thicker, but, in that case all of the walls in the container will also be thicker which is actually unnecessary, adding to the cost of the sterile container, as well as its bulk, and complicating the vacuum forming process. Hence, it is desirable to provide a sterile container at minimum cost and thickness and maximum strength to prevent contamination of the sterile articles which are used in the procedure.

BRIEF DESCRIPTION OF THE INVENTION

In accordance with the present invention, a package includes a container having an inner surface, an outer surface, and a sidewall defining a cavity having an opening to the exterior of the container. The container has an inner support tab in the cavity defining a recess in the outer surface of the container. A stiffening material is placed in the recess to add strength to the support locking tab. The support tab or tabs support an article or product disposed in the container. In a preferred form, the package of which the container is a part is sterile, and retains sterile articles for use in a medical procedure. Such sterility is achieved by the inclusion of a removable seal member covering and sealing the opening in the container. In a preferred form, the seal member is permeable to a sterilization gas and impermeable to the passage of bacteria.

FEATURES AND ADVANTAGES OF THE INVENTION

A principle feature of the present invention is the provision of an improved sterile package.

A feature and advantage of the invention is that outer recesses of the locking or support tabs are filled with a stiffening material.

Another feature and advantage of the invention is that the stiffened locking or support tabs are much more resistent to tear or rupture of the container in the region of the locking or support tabs than when they are left unstiffened.

Yet another feature and advantage of the invention is that the stiffened locking or support tabs reduce the likelihood that the sterile barrier of the package will be compromised during normal handling.

A further feature and advantage of the invention is that the walls of the container may be made of a reduced thickness to minimize the cost and bulk of the package without thereby compromising the strength and survivability of the package.

These and many other features and advantages of the present invention will become apparent to those of ordinary skill in the art from a consideration of the drawings and ensuing description of the invention.

DETAILED DESCRIPTION OF A PREFERRED EMBODIMENT

Figure 1:
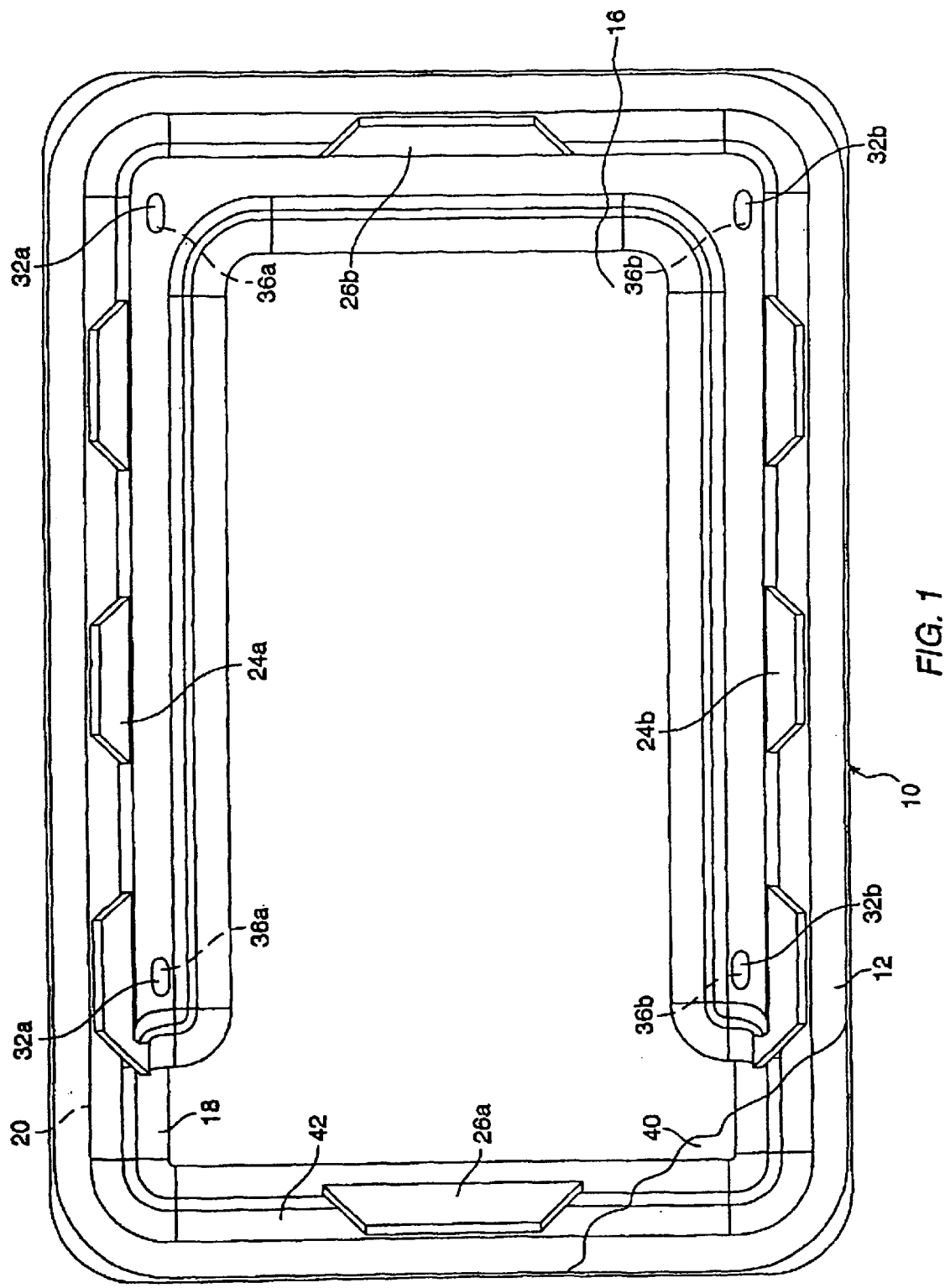
FIG. 1 is a plan view of a container in accordance with a presently preferred embodiment of the present invention.

Those of ordinary skill in the art will realize that the following description of the present invention is illustrative only and not in any way limiting. Other embodiments of the invention will readily suggest themselves to such skilled persons.

Referring now to FIGS. 1, 2, 3, 4 and 5, there is shown a package generally designated 10 having a container 12 and a tray 14 which is received in a cavity 16 of the container 12. Although it is preferred that the package 10 be rendered sterile for use in medical procedures, it is understood that the package need not be sterile for other uses.

Figure 2:
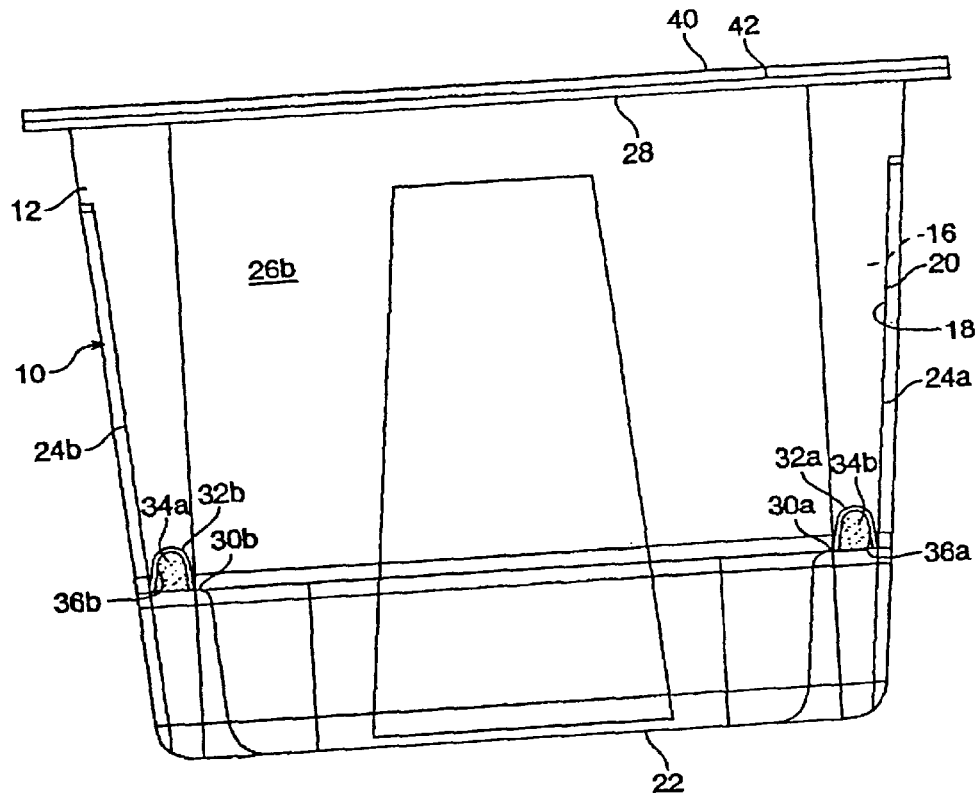
FIG. 2 is an end elevational view of the container of FIG. 1.
Figure 5:
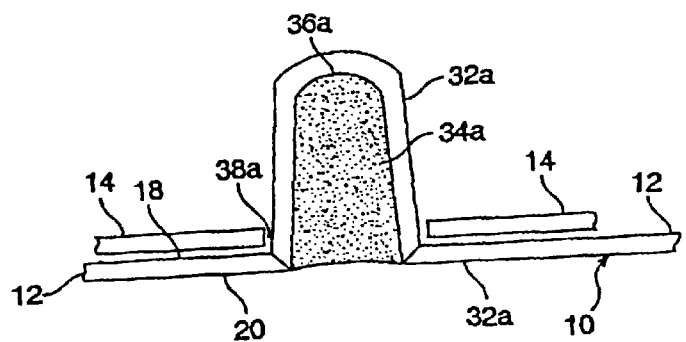
FIG. 5 is a fragmentary sectional view showing a filled locking or support tab of the container of FIGS. 1 and 2 and corresponding opening or slot of the tray of FIGS. 3 and 4 in accordance with a presently preferred embodiment of the present invention.

With reference to FIGS. 1, 2, and 5, the container 12 is preferably vacuum formed from a thermoplastic material, such as styrene with about 5–7% rubber. Those of ordinary skill in the art will realize that other materials can readily be substituted. The container 12 has an inner surface 18, an outer surface 20, and an inner bottom wall 22. The container 12 in accordance with this preferred embodiment has a pair of opposed sidewalls 24a and 24b connected to the inner bottom wall 22, and a pair of opposed end walls 26a and 26b connected to said inner wall 22 and sidewalls 24a and 24b to define the inner sterile cavity 16 communicating with an outer opening 28 in the container 12.

The container sidewalls 24a and 24b have a pair of corresponding opposed inner ledges 30a and 30b spaced from the inner bottom wall 22, and a pair of upstanding locking or support tabs 32a and 32b on the ledges 30a and 30b, respectively, and projecting into the cavity 16, as shown in FIG. 2. The locking tabs 32a and 32b naturally correspond with a plurality of recesses 34a and 34b in the outer surface 20 of the ledges 30a and 30b. The recesses 34a and 34b are filled in accordance with the invention with a stiffening agent or material 36a and 36b, such as a curable epoxy filler or other hardenable material which may be injected into the recessed 34a and 34b. This is done in order to enhance the rigidity and strength of the locking tabs 32a and 32b to prevent rupture or tearing of the locking tabs 32a and 32b, resulting in loss of sterility in the inside of the package 10 and container 12.

The introduction of the stiffening agent 36a and 36b to the outside of container 12 avoids the possibility of locking contaminants into a matrix within the sterile container. Any contaminants associated with the stiffening agent are isolated from the contents of the package 10 by the wall of the container at the recess.

Figure 4:
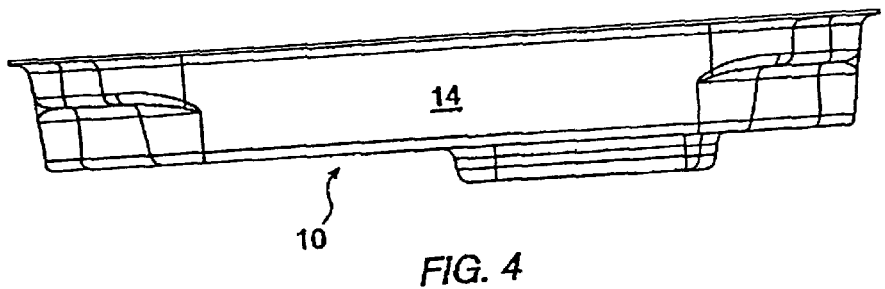
FIG. 4 is an end elevational view of the tray of FIG. 3.
Figure 3:
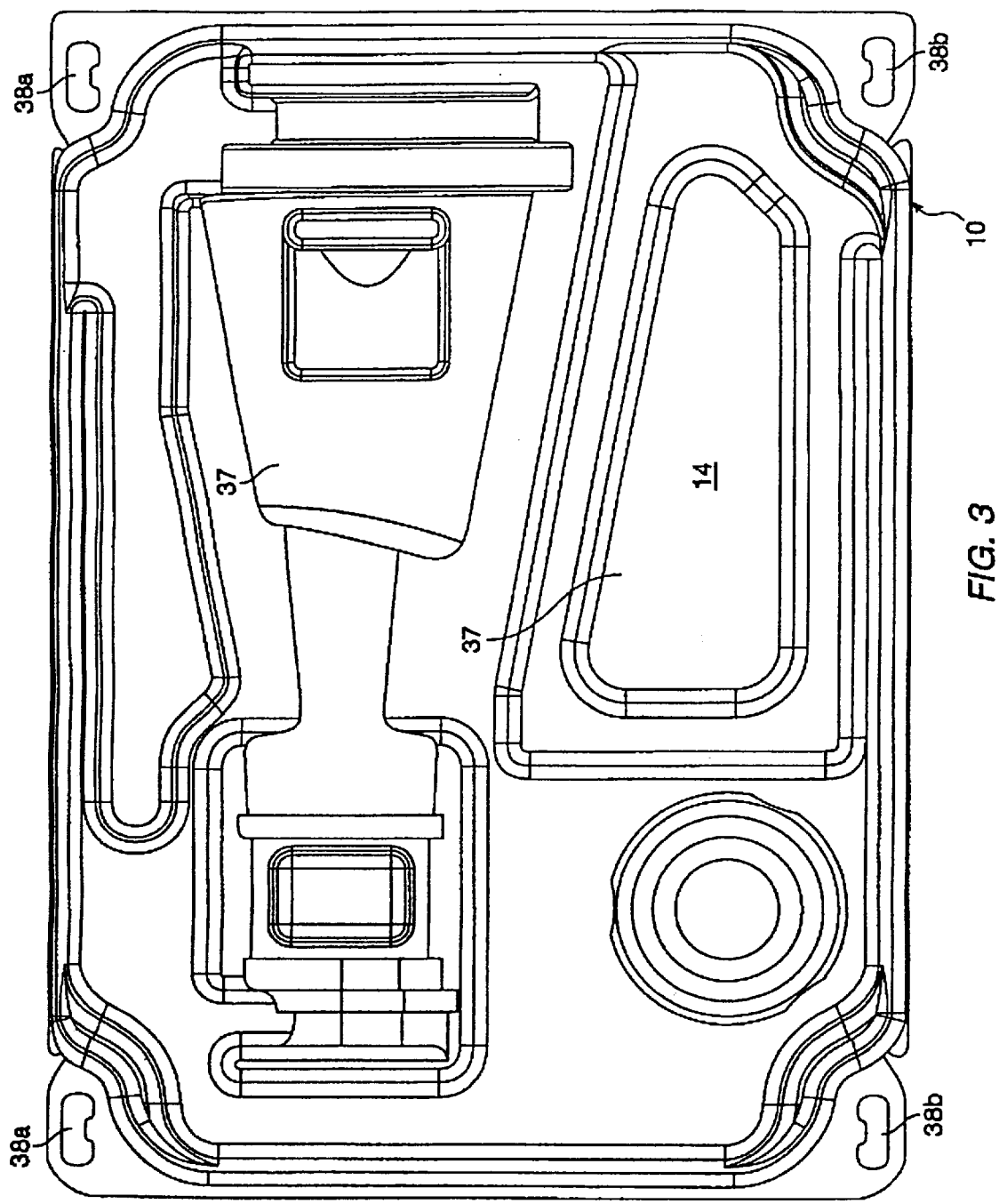
FIG. 3 is a plan view of a tray for use in a container in accordance with a presently preferred embodiment of the present invention.

With reference to FIGS. 3, 4, and 5, the sterile tray 14 is removably received in the cavity 16 of the container 12, and has a plurality of recesses 37 to retain sterile articles therein, such as parts used in a blood reoxygenator and purifier. The tray 14 has a plurality of openings 38a and 38b which register and engage with the locking tabs 32a and 32b when the tray 14 is placed on the ledges 30a and 30b in the cavity 16 to receive the locking tabs 32a and 32b and releasably retain the tray 14 at a desired position in the cavity 16. The tray 14 is spaced from the inner bottom wall 22 in order to provide room for a sterile component intermediate the tray 14 and inner wall 22, such as for the blood reoxygenator and purifier and tubing associated therewith. The tray 14 may be constructed from the same vacuum formed material as the container 12.

As shown in FIGS. 1 and 2, the package 10 has a cover 40 releasably sealed to an outer outwardly directed flange 42 of the container 12, with the flange 42 extending peripherally around the container 12. The cover 40 is permeable to the passage of a sterilizing gas and is impermeable to the passage of bacteria. The cover 40 may be constructed from a sheet termed TYVEK®, a product of E.I. Dupont deNemours, Wilmington, Del. Those of ordinary skill in the art will readily realize that other materials could also be used.

Thus, the articles are placed in the recesses 37 of the tray 14, and the component is placed on the inner bottom wall 22. The tray 14 is then placed on the ledges 30a and 30b of the container 12. Next, the cover 40 is sealed to the container flange 42, and the inside of the container 12 is sterilized by passing a sterilization gas, such as ethylene oxide, through the cover 40 in order to render the articles and component sterile, in addition to the container cavity 16 and tray 14. At the time of use, the cover 40 is removed from the container 12 in order to expose the articles and component in a sterile condition for use in a medical procedure.

Thus, in accordance with the present invention, the locking tabs 32a and 32b are strengthened in order to prevent rupture or tearing of the locking tabs 32a and 32b which may cause contamination to the inside of the package 10. As a result, a thinner wall may be used for the container 12 without jeopardizing the sterile barrier of the package 10 in order to reduce the cost and bulk of the package 10.

While embodiments and applications of this invention have been shown and described, it would be apparent to those skilled in the art that many more modifications than mentioned above are possible without departing from the inventive concepts herein. The invention, therefore, is not to be restricted except in the spirit of the appended claims. It is particularly to be understood that the present invention is applicable to non-sterile applications, and is useful wherever a strengthened support tab or support member is needed in a vacuum formed plastic item.

What is claimed is:

1. A sterile package, comprising:

a container having an inner surface, an outer surface, and a sidewall defining a cavity communicating with an outer opening, said container having a peripheral ledge in said cavity, and a plurality of spaced inner locking tabs on said inner surface of said ledge in said cavity, said locking tabs defining a recess in the outer surface of said ledge being filled with a filler material to enhance rigidity and strength of said locking tabs to prevent rupture of said locking tabs and loss of sterility in the inside of said package; and a tray being removable received in said cavity having recesses to retain sterile articles therein, said tray having a plurality of openings which register with said locking tabs when said tray is positioned on said ledge in said cavity to receive said locking tabs and releasably retain the tray at a desired position in said cavity.

2. The package of claim 1 wherein the filler material comprises an epoxy.

3. The package of claim 1 further comprising a cover releasably secured to an outer end of said container to close said cavity.

4. The package of claim 3 wherein said cover is permeable to passage of a sterilization gas and impermeable to the passage of bacteria.

5. The package of claim 4 wherein said sterilization gas comprises ethylene oxide.

6. The package of claim 1 wherein said container and tray comprise a thermally formed plastic material.

7. The package of claim 1 wherein said container is vacuum formed.

8. The package of claim 7 wherein said tray is vacuum formed.

9. A sterile package, comprising:

a container having a substantially uniform thickness and having an inner surface, an outer surface, an inner wall, a pair of opposed sidewalls connected to said inner wall, and a pair of opposed end walls connected to said inner wall and said sidewalls defining an inner sterile cavity communicating with an outer opening, said sidewalls having a pair of opposed inner ledges spaced from said inner wall, and a pair of spaced upstanding locking tabs on the ledge of each sidewall projecting into said cavity, said locking tabs forming a plurality of recesses in the outer surface of said ledges being filled with a filler material to enhance rigidity and strength of said locking tabs to prevent rupture of said locking tabs and loss of sterility in the inside of said package;

a sterile tray being removably received in said cavity and having recesses to retain sterile articles therein, said tray having a plurality of openings which register with said locking tabs when said tray is positioned on said ledge in said cavity to receive said locking tabs and releasably retain said tray at a desired position in said cavity, said tray being spaced from said inner wall to place a sterile component intermediate said tray and inner wall; and a cover releasably secured to an outer end of said package, said cover being permeable to the passage of a sterilizing gas and being impermeable to the passage of bacteria, such that said cover may be removed at the time of a medical procedure to expose said sterile articles and component.

10. The package of claim 9 in which the container has an outwardly directed outer flange extending peripherally around the container, and in which the cover is releasably sealed to said flange.

11. A method of making a sterile package comprising the steps of:

forming a container having a peripheral ledge in a cavity and a plurality locking tabs on said ledge defining a corresponding recess in an outer surface of the container;

filling said recesses with a filler material to add rigidity to said locking tabs;

forming a tray having a plurality of recesses to receive articles therein and a plurality of openings which register with said locking tabs;

placing said tray in said cavity with said locking tabs being received in said openings;

closing an outer end of the container with a cover which is permeable to a sterilization gas; and subjecting the package to said sterilization gas which passes through said cover to sterilize said cavity, tray, and articles therein.

12. A method of making a sterile package comprising the steps of:

forming a container having a plurality of walls defining a cavity and having an inner peripheral ledge in the cavity, and a plurality of upstanding locking tabs on said ledge defining a corresponding recess in an outer surface of the container;

filling said recesses with a filler material to enhance the strength and rigidity of the locking tabs in the cavity;

forming a tray having a plurality of recesses to receive articles therein and a plurality of openings which register with said locking tabs;

placing said tray in said cavity with said locking tabs received in the openings at a location spaced from an inner wall of said container;

closing an outer end of said container with a cover which is permeable to the passage of a sterilization gas, and impermeable to the passage of bacteria, said cover releasably closing said cavity; and passing a sterilization gas through said cover to sterilize said cavity, tray and articles therein.

13. A package, comprising:

a container having an inner surface, an outer surface, and a sidewall defining a cavity communicating with an outer opening, said container having a peripheral ledge in said cavity, and a plurality of spaced inner locking tabs on said inner surface of said ledge in said cavity, said locking tabs defining a recess in the outer surface of said ledge being filled with a filler material to enhance rigidity and strength of said locking tabs; and a tray being removable received in said cavity having recesses to retain articles therein, said tray having a plurality of openings which register with said locking tabs when said tray is positioned on said ledge in said cavity to receive said locking tabs and releasably retain the tray at a desired position in said cavity.

14. The package of claim 13 wherein the filler material comprises an epoxy.

15. The package of claim 13 further comprising a cover releasably secured to an outer end of said container to close said cavity.

16. The package of claim 15 wherein said cover is permeable.

17. The package of claim 13 wherein said container and tray comprise a thermally formed plastic material.

18. The package of claim 13 wherein said container is vacuum formed.

19. The package of claim 18 wherein said tray is vacuum formed.

20. A package, comprising:

a container having a substantially uniform thickness and having an inner surface, an outer surface, an inner wall, a pair of opposed sidewalls connected to said inner wall, and a pair of opposed end walls connected to said inner wall and said sidewalls defining an inner cavity communicating with an outer opening, said sidewalls having a pair of opposed inner ledges spaced from said inner wall, and a pair of spaced upstanding locking tabs on the ledge of each sidewall projecting into said cavity, said locking tabs forming a plurality of recesses in the outer surface of said ledges being filled with a filler material to enhance rigidity and strength of said locking tabs;

a tray being removably received in said cavity and having recesses to retain articles therein, said tray having a plurality of openings which register with said locking tabs when said tray is positioned on said ledge in said cavity to receive said locking tabs and releasably retain said tray at a desired position in said cavity, said tray being spaced from said inner wall to place a component intermediate said tray and inner wall; and a cover releasably secured to an outer end of said package.

21. The package of claim 20 in which the container has an outwardly directed outer flange extending peripherally around the container, and in which the cover is releasably sealed to said flange.

22. A method of making a package comprising the steps of:

forming a container having a peripheral ledge in a cavity and a plurality of locking tabs on said ledge defining a corresponding recess in an outer surface of the container;

filling said recesses with a filler material to add rigidity to said locking tabs;

forming a tray having a plurality of recesses to receive articles therein and a plurality of openings which register with said locking tabs;

placing said tray in said cavity with said locking tabs being received in said openings;

closing an outer end of the container with a cover.

23. A method of making a package comprising the steps of:

forming a container having a plurality of walls defining a cavity and having an inner peripheral ledge in the cavity, and a plurality of upstanding locking tabs on said ledge defining a corresponding recess in an outer surface of the container;

filling said recesses with a filler material to enhance the strength and rigidity of the locking tabs in the cavity;

forming a tray having a plurality of recesses to receive articles therein and a plurality of openings which register with said locking tabs;

placing said tray in said cavity with said locking tabs received in the openings at a location spaced from an inner wall of said container;

closing an outer end of said container with a cover, said cover releasably closing said cavity.

* * * * *